United States Patent
Cooke

(10) Patent No.: US 9,345,908 B2
(45) Date of Patent: May 24, 2016

(54) TREATMENT BALLOON WITH BEAM POSITION DETECTOR

(71) Applicant: Empire Technology Development LLC, Wilmington, DE (US)

(72) Inventor: Cameron Cooke, Sydney (AU)

(73) Assignee: Empire Technology Development LLC, Wilmington, DE (US)

( * ) Notice: Subject to any disclaimer, the term of this patent is extended or adjusted under 35 U.S.C. 154(b) by 210 days.

(21) Appl. No.: 13/978,109

(22) PCT Filed: Sep. 27, 2012

(86) PCT No.: PCT/US2012/057535
§ 371 (c)(1),
(2) Date: Jul. 2, 2013

(87) PCT Pub. No.: WO2014/051589
PCT Pub. Date: Apr. 3, 2014

(65) Prior Publication Data
US 2014/0187848 A1    Jul. 3, 2014

(51) Int. Cl.
| | |
|---|---|
| *A61N 5/10* | (2006.01) |
| *G01T 3/06* | (2006.01) |
| *G01T 1/20* | (2006.01) |
| G01T 1/203 | (2006.01) |
| G01T 1/22 | (2006.01) |

(52) U.S. Cl.
CPC ............ *A61N 5/1067* (2013.01); *A61N 5/1002* (2013.01); *G01T 1/203* (2013.01); *G01T 1/22* (2013.01); *G01T 3/06* (2013.01)

(58) Field of Classification Search
CPC ..... A61N 5/00; A61N 5/1049; A61N 5/1002; A61N 5/1067; G01T 3/06; G01T 1/203; G01T 1/22
See application file for complete search history.

(56) References Cited

U.S. PATENT DOCUMENTS

| | | |
|---|---|---|
| 5,723,391 A | 3/1998 | Hunter |
| 6,520,959 B1 | 2/2003 | Iwahashi et al. |

(Continued)

FOREIGN PATENT DOCUMENTS

WO    2007040392 A2    4/2007

OTHER PUBLICATIONS

Axelsson, J. et al., "Cernekov emission induced by external beam radiation stimulates molecular flouresence", American Association of Physicists in Medicine. 2011, p. 4127-4132.

(Continued)

*Primary Examiner* — David J Makiya
*Assistant Examiner* — Dani Fox
(74) *Attorney, Agent, or Firm* — Moritt Hock & Hamroff LLP; Steven S. Rubin, Esq.

(57) ABSTRACT

Techniques are generally described for a treatment balloon, and methods and systems effective to detect a position of a beam. The system may include a treatment balloon effective to receive the beam. The treatment balloon may include a shaft and a balloon portion with an open end in communication with the shaft. The balloon portion may be effective to be at least partially filled with a fluid. The treatment balloon may be effective to generate a light wave when the treatment beam is incident on the treatment balloon. A waveguide in the treatment balloon may be effective to receive the light wave. A light detector in optical communication with the waveguide may be effective to detect the light wave. A processor in communication with the light detector may be effective to detect the position of the beam.

34 Claims, 6 Drawing Sheets

(56) References Cited

U.S. PATENT DOCUMENTS

| | | | |
|---|---|---|---|
| 6,635,052 | B2 | 10/2003 | Loeb |
| 6,993,376 | B2 * | 1/2006 | Testardi .................. 600/478 |
| 7,112,195 | B2 | 9/2006 | Boll et al. |
| 7,297,914 | B2 | 11/2007 | Pang |
| 8,007,444 | B2 | 8/2011 | Kokate et al. |
| 2002/0188204 | A1 | 12/2002 | McNamara et al. |
| 2006/0025799 | A1 | 2/2006 | Basu |
| 2008/0027416 | A1 | 1/2008 | Hamel et al. |
| 2009/0218495 | A1 | 9/2009 | Leroux et al. |
| 2009/0227998 | A1 | 9/2009 | Aljuri et al. |
| 2010/0019170 | A1 | 1/2010 | Hart et al. |
| 2010/0145379 | A1 * | 6/2010 | Isham ..................... 606/192 |
| 2010/0288934 | A1 * | 11/2010 | Keppel et al. ............ 250/362 |
| 2011/0184391 | A1 | 7/2011 | Aljuri et al. |
| 2012/0123185 | A1 | 5/2012 | Isham |

OTHER PUBLICATIONS

Ross, H. H., "Measurement of β-emitting nuclide using Cerenkov radiation", Analytical Chemistry, 1969, p. 1260-1265.

I E. Tamm and I. M Frank "Coherent radiation from a fast electron in a medium", Dokl. Akad. Nauk SSSR, 1937, 7 pages.

Lee, B. et al., "Characterization of One-dimensional Fiber-optic Scintillation Detector for Electron Beam Therapy Dosimetry", Analytical Chemistry, 1969, 1408-1411.

S. H. Law , N. Suchowerska, D. D. McKenzie, S. C. Flemming "Cerenkov radiation in optical fibers", ACOFT/ALOS 2006-Proceedings, 2006, p. 100-102.

Mead, C. A. "Quantum Theory of the Refractive Index", Physical Review, 1958, 359-369.

Cernekov, P.A. "Visible Radiation Produced by Electrons Moving in a medium with Velocities Exceeding that of Light", Physical Review 1937, 378-380.

Brichard B et al "Fiber-optic gamma-flux monitoring in a fission reactor by means of Cernekov radiation", Measurement Science and Technology 2007, p. 3257-3262.

International Search Report and Written Opinion for PCT application with application No. PCT/US12/57535, dated Apr. 11, 2013, 13 pages.

Wolfe W. L. "Introduction to Imaging Spectrometers" SPIE Optical Engineering Press, 1997, 1 page.

"Optical Fibers", Wikipedia, 2012, retrieved from wikipedia.org, 23 pages.

"Endoscope Overview 2008", EVIS EXERA II, Olympus 2008, retrieved from http://www.ivermedi.com/attachments/pdf/olympus, 6 pages.

"Prostate Cancer", Wikipedia, 2012, retrieved from http://en.wikipedia.org, 16 pages.

Kupelian, P. A. et al., "Comparison of the efficacy of local therapies for localized prostate cancer in the prostate-specific antigen era: a large single-institution experience with radical prostatectomy and external-beam radiotherapy", J. Clin. Oncol., 2002, 3376-3385, 20 (16).

Lawton, C. A. et al., "Long-term treatment sequelae following external beam irradiation for adenocarcinoma of the prostate: analysis of RTOG studies 7506 and 7706" Int. J Radiat Oncol Biol Phys, 1991, 935-939, 21 (4).

Brenner, D. J. et al., "Second malignancies in prostate carcinoma patients after radiotherapy compared with surgery" Cancer, 2000, 398-406, 88 (2).

"Home", diamondAnvils.com, downloaded Oct. 17, 2013, 2 pages.

Siegel, R. et al., "Cancer statistics, 2011: the impact of eliminating socioeconomic and racial disparities on premature cancer deaths." CA Cancer J Clin, 2011, 212-236, 61.

Hong, H. et al., "Positron emission tomography imaging of prostate cancer". Amino Acids, 2009, 29 pages, 39 (1).

Braun, K. et al., "High-Resolution Flow Cytometry: a Suitable Tool for Monitoring Aneuploid Prostate Cancer Cells after TMZ and TMZ-BioShuttle Treatment". Int J Med Sci. 2009, 338-347, 6 (6).

Peyromaure M, Valri A, Rebillard X, Beuzeboc P, Richaud P, Souli M, Salomon L "[Characteristics of prostate cancer in men less than 50-year-old]" Prog. Urol., 2009, 803-809, 19 (11).

Jemal, A. et al., "Cancer statistics, 2005" CA Cancer J Clin, 2005, p. 10-30, 55 (1).

"What Are the Risk Factors for Prostate Cancer?" American Cancer Society, 2012, retrieved from http://www.cancer.org/cancer/prostatecancer/detailedguide/, 85 pages.

Cross, A. J. et al., "A Prospective Study of Meat and Meat Mutagens and Prostate Cancer Risk", American Association for Cancer Research, cancerres.aacrjournals.org, 2005, 7 pages.

Gray, H., Anatomy of the Human Body, 1918, 1 page.

Livadas, K. E. et al., "Ureteroscopic Removal of Mildly Migrated Stents Using Local Anesthesia Only", Second Department of Urology, Athens Medical School, Sismanoglio Hospital, Athens, Greece, 2007, p. 1998-2001.

Park, H. K et al., "Ureteroscopic Lithotripsy under Local Anesthesia: Analysis of the Effectiveness and Patient Tolerability", European Urology, 2004, 670-673, 45.

Schuster, T. G. et al., "Complications of Ureteroscopy: Analysis of Predictive Factors", Section of Urology, University of Michigan, Ann Arbor, Michigan, Journal of Urology,2005, 538-540.

J. D. Slater et al, "Proton therapy for prostate cancer; the initial Loma Linda University experience", Int. J. Radiat. Oncol. Biol. Phys 59, 2004, 348-352.

A. L. Zietman et al, Comparisons of conventional-dose vs high-dose conformal radiation therapy in clinically localized adenocarcinoma of the prostate: a randomized controlled trial, J. A. M. A., 2005, 294 (10, 1233-1239).

R. deCrevoisier et al, "Increased risk of biochemical and local failure in patients with distended rectum on the planning CT for prostate cancer radiotherapy," Int. J. Radiat. Oncol. Biol. Phys., 2005, p. 965-97362, (4).

Lambert et al. "Intrafractional motion during proton beam scanning" Phys. Med. Biol., 2005, 853-4862, 50.

Thomas E. Byrne, "A Review of Prostate Motion with Considerations for the Treatment of Prostate Cancer", Medical Dosimetry 30(3), 2005, pp. 155-161.

"Proton Therapy", Wikipeida, retrieved from wikipedia.com, Aug. 15, 2013, 9 pages.

"An organization for those interested in proton, light ion and heavy charged particle radiotherapy", Particle Therapy Co-Operative Group, retrieved from http://www.ptcog.com/, downloaded on Oct. 18, 2013, 2 pages.

Hardcastle, N. et al., In vivo real-time rectal wall dosimetry for prostate radiotherapy, Physics in medicine and biology, 2010, pp. 3859-3871, 55(13).

Robert Jan Smeenk,Bin S. Teh,E. Brian Butler,Emile N.J.Th. van Lin,Johannes H.A.M. Kaanders. "Is there a role for endorectal balloons in prostate radiotherapy? A systematic review" Journal of the European Society for Theraputic Radiology and Oncology, 2010, p. 1-6.

"Qfix Systems", retrieved from qfix.com/, downloaded Oct. 17, 2013, 1 page.

Wang, Ken Kang-Hsin, Ph.D et al., "A Study to Quantify the Effectiveness of Daily Endorectal Balloon for Prostate Intrafraction Motion Management", Presented in part at the 52nd American Society of Radiation Oncology Annual Meeting on Nov. 1, 2010, 1055-1063.

Melancon, A. D., "Range Adaptive Proton Therapy for Prostate Cancer", 2010, UT GSBS Dissertations and Theses (Open Access), Paper 44, 172 pages.

"Cancer Therapy", Particle Therapy Cancer Research Institute University of Oxford 2012, 2 pages.

Dong, Lei, PHD and Andrew Lee, MD, MPH, "Prostate Cancer Proton Therapy Initial Experience at MDACC PTCH", retrieved from ptcog.web.psi.ch/PTCOG45/Tuesday%20Talks/53ALEE.pdf, downloaded Aug. 15, 2013, 48 pages.

Rasmussen SN, Riis P, "Rectal wall thickness measured by ultrasound in chronic inammatory diseases of the colon", Scand J Gastroenterol, Jan. 1985, p. 109-14, 20(1).

In Vivo Dosimetry During Prostate Cancer Radiotherapy, ClinicalTrials.gov, Mar. 2011, retrieved from clinicaltrials.gov/ct2/show/NCT01307852, 3 pages.

* cited by examiner

TREATMENT BALLOON WITH BEAM POSITION DETECTOR

CROSS REFERENCE TO RELATED APPLICATION

This application is a U.S. National Stage filing under 35 U.S.C. §371 of International Application No. PCT/US12/57535 filed Sep. 27, 2012, the entirety of which is hereby incorporated by reference.

BACKGROUND

Unless otherwise expressly indicated herein, none of the material presented in this section is prior art to the claims of this application and is not admitted to be prior art by having been included herein.

During treatment of prostate cancer, a treatment balloon may be used to stabilize a position of the prostate. The treatment balloon may include a shaft and a balloon portion with an open end in communication with the shaft. When the treatment balloon is used, the shaft may be inserted into a patient's rectum and the balloon portion may be inflated. The inflated balloon portion may stabilize a position of the prostate during treatment.

SUMMARY

In one example, a method for detecting a position of a beam is generally described. The method may include receiving the beam by a treatment balloon. The treatment balloon may include a shaft and a balloon portion with an open end in communication with the shaft. The balloon portion may be effective to be at least partially filled with a fluid. The treatment balloon may be effective to generate a light wave when the treatment beam is incident upon the treatment balloon. The method may further include receiving the light wave by a waveguide in the treatment balloon. The method may further include detecting the light wave by a light detector in optical communication with the waveguide. The method may further include detecting the position of the beam by a processor in communication with the light detector.

In one example, a treatment balloon is generally described. The treatment balloon may include an opaque shaft. The treatment balloon may include an opaque balloon portion with an opening in communication with the shaft. The balloon portion may be effective to be at least partially filled with a fluid. The treatment balloon may include at least one waveguide in the treatment balloon. The treatment balloon may include a light detector in optical communication with the waveguide. The light detector may be effective to receive and detect light from the waveguide.

In one example a system effective to detect a position of a beam is generally described. The system may include a treatment balloon effective to receive the beam. The treatment balloon may include a shaft and a balloon portion with an open end in communication with the shaft. The balloon portion may be effective to be at least partially filled with a fluid. The treatment balloon may be effective to generate a light wave when the treatment beam is incident on the treatment balloon. A waveguide may be in the treatment balloon. The waveguide may be effective to receive the light wave. The system may include a light detector in optical communication with the waveguide. The light detector may be effective to detect the light wave. The system may further include a processor in communication with the light detector. The processor may be effective to detect the position of the beam.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

DETAILED DESCRIPTION

Figure 1:
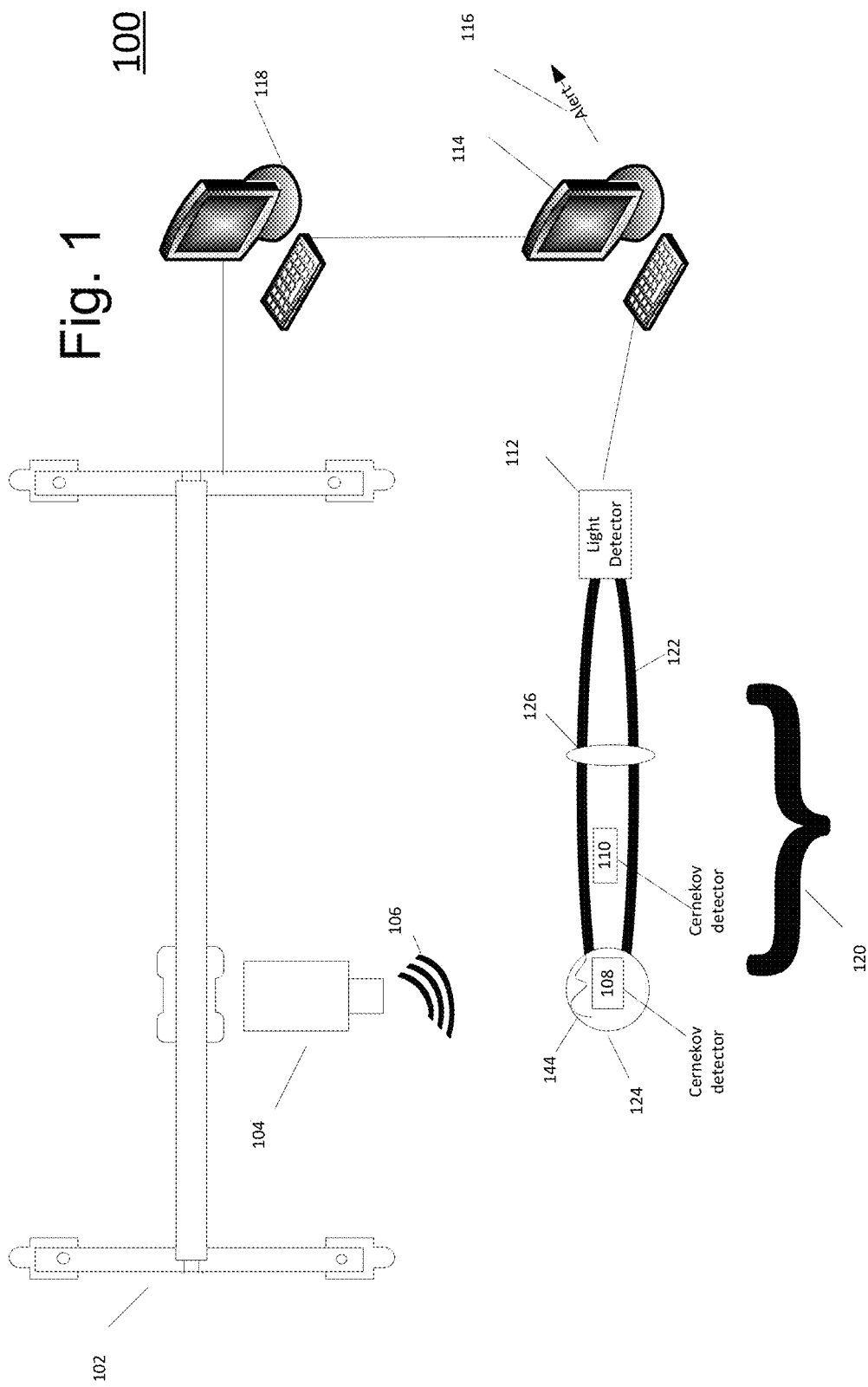
FIG. 1 is a system diagram illustrating an example treatment balloon with beam position detector.

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

This disclosure is generally drawn, inter alia, to devices, apparatus, systems and methods relating to a treatment balloon with beam position detector.

Briefly stated, technologies are generally described for a treatment balloon, and methods and systems effective to detect a position of a beam. The system may include a treatment balloon effective to receive the beam. The treatment balloon may include a shaft and a balloon portion with an open end in communication with the shaft. The balloon portion may be effective to be at least partially filled with a fluid. The treatment balloon may be effective to generate a light wave when the treatment beam is incident on the treatment balloon. A waveguide in the treatment balloon may be effective to receive the light wave. A light detector in optical communication with the waveguide may be effective to detect the light wave. A processor in communication with the light detector may be effective to detect the position of the beam.

FIG. 1 is a system diagram illustrating an example treatment balloon with beam position detector according to at least some embodiments described herein. In some examples, a beam position detector 100 may include a gantry 102, a treatment source 104, a treatment balloon 120, a light detector 112, a processor 114 and/or a processor 118. Treatment balloon 120 may include a shaft 122 and a balloon portion 124. An open end of balloon portion 124 may be in communication with shaft 122. Light detector 112, processor 114, processor 118 and/or gantry 102 may be configured to be in communication such as through a wired or wireless network.

In use, treatment balloon 120 may be inserted into a patient's urethra or rectum. Balloon portion 124 may be fully or partially filled with a fluid 144 to limit a movement of the patient's prostate. A migration stopper 126 may be used to limit movement of treatment balloon 120 after insertion. Treatment balloon 120 may be an endorectal balloon. As discussed in more detail below, treatment source 104 may generate a treatment beam 106 that may be used to treat a tumor in the prostate. Balloon portion 124 may include a Cernekov detector 108 and shaft 122 may include a Cernekov detector 110. Cernekov detectors 108, 110 may be effective to detect light generated when beam 106 travels through portions of treatment balloon 120 faster than the speed of light in that material. Light detector 112 may receive light from Cernekov detectors 108, 110 and generate electrical signals in response. The electrical signals may be processed by processor 114 to detect a position of beam 106. In response to the detection, processor 114 may generate an alert 116. Processor 114 may also, or alternatively, communicate with processor 118 to control a movement of gantry 102 to move gantry 102, and beam 106, to a different position or stop beam 106. Processor 114 may detect that beam 106 has been at the correct position for a long enough period of time so that less dosage of beam 106 may be used. Conversely, processor 114 may detect that beam 106 has not been at the correct position for a long enough period of time so that more dosage of beam 106 should be used.

Cernekov photons and light waves may be generated when a charged particle moves faster than the speed of light in a given medium. A threshold condition for the generation of the lights waves may be given by $$\beta n > 1 \quad \text{(Eq. 1)}$$

where n is the refractive index of the medium and $$\beta = \left[1 - \left(\frac{1}{\frac{E_{(keV)}}{511} + 1}\right)^2\right]^{\frac{1}{2}} \quad \text{(Eq. 2)}$$

In an example, with an average electron energy of 1 MeV, β may be 0.94 and a value of n over 1.06 may result in the generation of Cernekov photons. An optical fiber, which may be used as discussed below, may have an n in the core of 1.52.

At a given wavelength λ, and assuming that particles maintain a constant velocity as they traverse a fiber, the intensity of the radiation may be given by $$I_{cap} = \text{Np} \frac{2\pi\rho^3}{\sin\gamma} \frac{e^2}{4\pi^2\varepsilon_0\lambda^2 c^2}\left(1 - \frac{c^2}{n_{co}^2 v^2}\right) \times \cos^{-1}\left(\frac{v(n_{co} - \Delta n) - c \times \cos\gamma}{\sin\gamma\sqrt{v^2 n_{co}^2 - c^2}}\right) \quad \text{(Eq. 3)}$$

and in the relativistic case $$I_{cap} = \text{Np} \frac{2\pi\rho^3}{\sin\gamma} \frac{e^2}{4\pi^2\varepsilon_0\lambda^2 c^2}\left(1 - \frac{1}{n_{co}^2}\right) \times \cos^{-1}\left(\frac{n_{co} - \Delta n - \cos\gamma}{\sin\gamma\sqrt{n_{co}^2}}\right) \quad \text{(Eq. 4)}$$

where Np is the number of particles, p is the fiber core radius, e is the charge on an electron, c is the speed of light in a vacuum, v is the speed of the particle, $n_{co}$ is the refractive index of the fiber core, Δn is the fiber core/cladding refractive index difference, εo is the permittivity of a vacuum, and γ is the angle between the possible track and the fiber axis in the direction of the detector.

Figure 2:
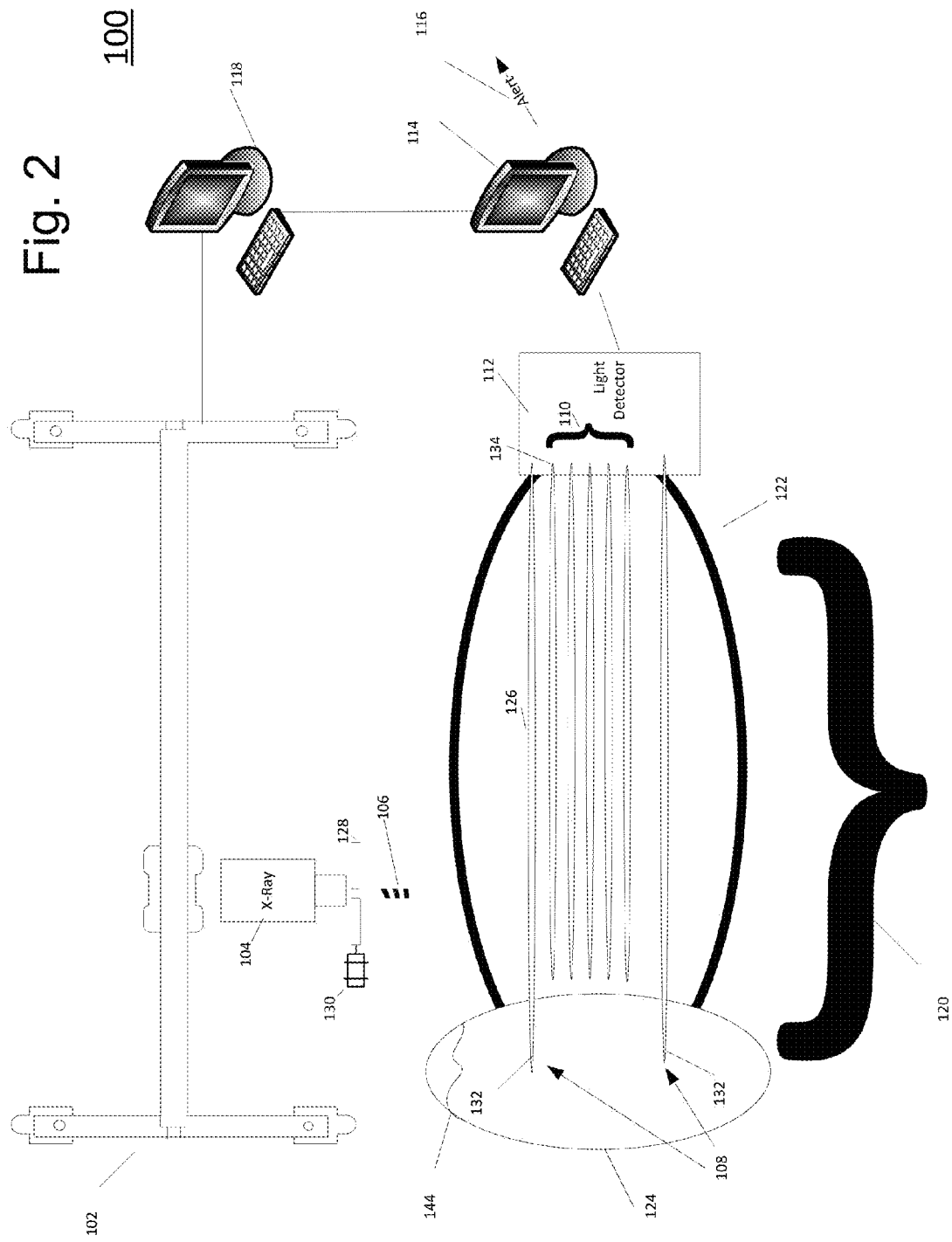
FIG. 2 is a system diagram illustrating an example treatment balloon with beam position detector.

FIG. 2 is a system diagram illustrating an example treatment balloon with beam position detector according to at least some embodiments described herein. Those components in FIG. 2 that are labelled identically to components of FIG. 1 will not be described again for the purposes of clarity.

In FIG. 2, treatment balloon 120 is shown further magnified to focus on additional details. In the example shown in FIG. 2, treatment source 104 may be an X-Ray source and beam 106 may be an X-Ray beam. One or more collimators 128 may be used to modulate a shape of beam 106. Collimators 128 may be steel plates that may be adjusted to produce a beam of any desired shape such as by control of a motor 130. Collimators 128 may be used to adjust a shape of beam 106 to correspond to the shape of a tumor. Collimators 128 may be implemented using a single plate with a hole bored therethrough.

Cernekov detector 108 may include one or more fiber optic waveguides 132. As discussed in more detail below, in examples where Cernekov photons are generated in balloon portion 124, such photons may generate a light wave. The light wave may travel down fiber optic waveguides 132 to light detector 112. Light detector 112 may receive and detect the light wave.

Cernekov detector 110 may include one or more fiber optic waveguides 134. As discussed in more detail below, in examples where Cernekov photons are generated in shaft 122, such photons may generate light waves that travel down fiber optic waveguides 134 to light detector 112. Light detector 112 may be in optical communication with waveguides 134 and may receive and detect the light waves.

Gantry 102 may be used to move around a patient so that beams 106 may be incident upon a tumor at multiple angles. As mentioned above, treatment balloon 120 may be inserted into a patient. Balloon portion 124 may be at least partially filled with water or another fluid 144 with an index of refraction greater than n as discussed above with reference to equations 1 and 2. The at least partially filled balloon may limit a movement of the patient's prostate. X-Ray beam 106 may be incident upon the patient's prostate, balloon portion 124, and/or shaft 122.

Light detector 112 may include, for example, photodiodes such as avalanche photodiodes. The photodiodes may be selected to have a relatively high sensitivity in the blue wavelength range—about 450 nm to about 495 nm. Light detector 112 may include photomultiplier tubes and/or charged coupled diodes.

Figure 3:
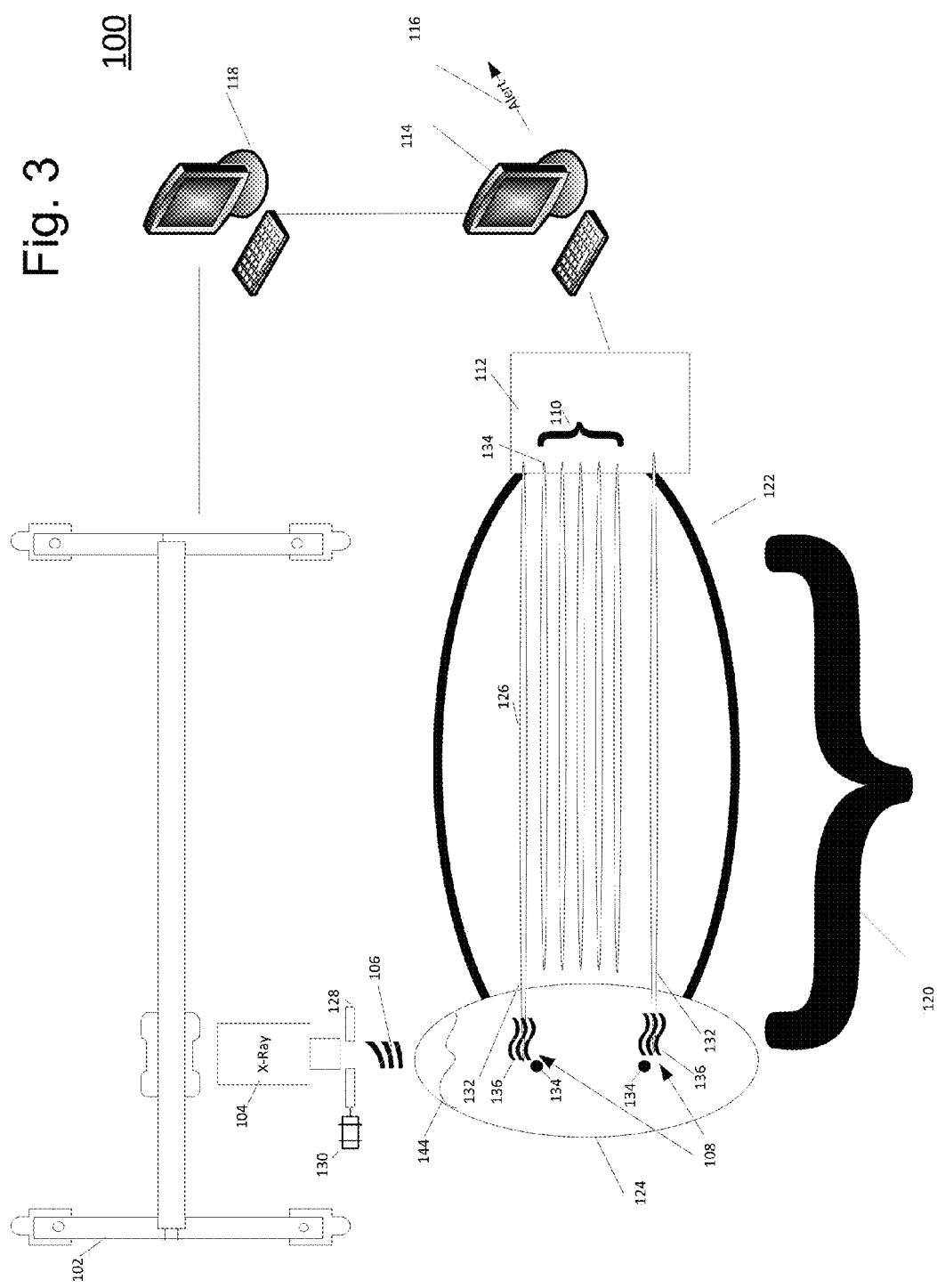
FIG. 3 is a system diagram illustrating an example treatment balloon with beam position detector.

FIG. 3 is a system diagram illustrating an example treatment balloon with beam position detector according to at least some embodiments described herein. Those components in FIG. 3 that are labelled identically to components of FIGS. 1 and 2 will not be described again for the purposes of clarity.

As balloon portion 124 is filed with a fluid 144 with an index of refraction greater than n as discussed above with reference to equations 1 and 2, Cernekov photons 134 may be generated in examples where beam 106 is incident upon balloon portion 124 and fluid 144. Cernekov photons 134 in turn, may generate light waves 136. Light waves 136 may travel down fiber optic waveguides 132 and may be detected by light detector 112. For example, light waves 136 may have a blue color and may have wavelengths of about 450 nm to about 495 nm.

Fiber optic waveguides 132 may be disposed at different locations inside balloon portion 124. An intensity of light waves 136 at each waveguide 132 may be detected by light detector 112 and so a relative position of beam 106 with respect to balloon portion 124 may be detected by processor 114 based on the intensities of waves 136. For example, processor 114 may compare a photon count from one waveguide 132 to the other waveguide 132 to estimate a position of beam 106. Waveguides 132 may thus be used, for example, to determine a position of beam 106 with respect to a sagittal plane of a patient depending on a positioning of waveguides 132.

Balloon portion 124 may be made of an opaque material so that stray visible light may be inhibited from entering balloon portion 124. Light detector 112 may be used to detect waves 136 before beam 106 is incident upon balloon portion 124 so that an ambient light may be calculated by processor 114. The ambient light may be subtracted from future calculations by processor 114 when beam 106 is applied. If ends of waveguides 132 are bent, a prism may be added to refract light waves from balloon portion 124 into waveguides 132.

Figure 4:
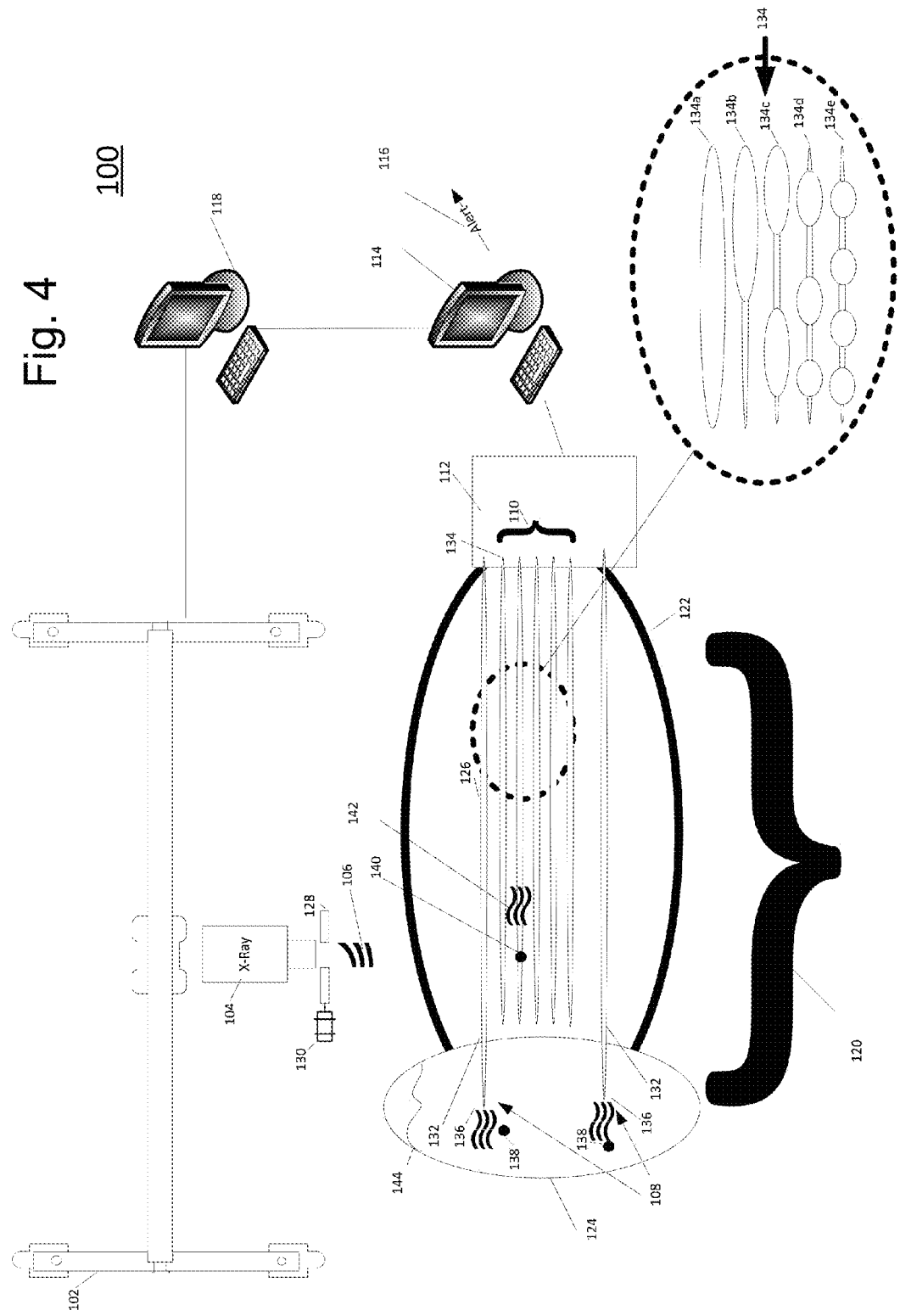
FIG. 4 is a system diagram illustrating an example treatment balloon with beam position detector.

FIG. 4 is a system diagram illustrating an example treatment balloon with beam position detector according to at least some embodiments described herein. Those components in FIG. 4 that are labelled identically to components of FIGS. 1, 2 and 3 will not be described again for the purposes of clarity.

As mentioned above, Cernekov detector 110 may include one or more waveguides 134. In examples where beam 106 is incident upon waveguides 134, Cernekov photons 140 may be generated as an index of refraction of waveguides 134 may be greater than n as discussed above with reference to equations 1 and 2. Cernekov photons 140 may, in turn, generate light waves 142. Light waves 142 may travel down waveguides 134 and be detected by light detector 112. Waveguides 134 may have a reflective cap at an end distal from light detector 112 so that waves which travel away from light detector 112 may be reflected back toward light detector 112.

As shown in the magnified view in FIG. 4, waveguides 134 may include waveguides 134a, 134b, 134c, 134d, and/or 134e. A number of photons per second in light wave 142 generated by Cernekov photon 140 may be proportional to a width of waveguide 134. Waveguides 134 may be modulated to have varying thick and thin sections, as shown for waveguides 134a, 134b, 134c, 134d, and 134e. By using waveguides with varying thicknesses, light detector 112 may be able to detect a position of beam 106 with respect to waveguides 134. Waveguides 134 may help detect a position in a patient's transverse plane and/or detect a more fine granularity of a position of beam 106. For example, each waveguide 134a, 134b, 134c, 134d, 134e may generate a different number of photons in light wave 142 in response to generation of Cernekov photon 140. Processor 114 may detect a position of beam 106 and how beam 106 is moving with respect to waveguides 134. For example, light detector 112 may be able to detect that beam 106 is incident upon a particular waveguide of waveguides 134 based on whether light is detected from the particular waveguide. Further, light detector 112 may be able to detect a position along the particular waveguide where beam 106 is incident based upon the number of photons per second output from the waveguide. A higher number of photons per second may indicate that the beam is incident on a relatively thicker section of the particular waveguide. A lower number of photons per second may indicate that the beam is incident on a relatively thinner section of the particular waveguide—or perhaps on both a thicker section and a thinner section. In the example, 5 waveguides 134a, 134b, 134c, 134d and 134e are shown and so a binary pattern with $2^5=32$ positions may be realized. Shaft 122 may be opaque to inhibit stray visible light from entering waveguides 134.

In an example, as beam 106 moves in position from waveguide 134e to waveguide 134d, less light photons per second may be generated in waveguide 134e and more light photons per second may be generated by waveguide 134d. Consequently, processor 114 may determine that beam 106 has moved from a position corresponding to waveguide 134e to a position corresponding to waveguide 134d.

Processor 114 may also determine a change in distance between shaft 122 and gantry 102. For example, processor 114 may determine a position of endpoints of waveguides 136, determine an angle between the endpoints and gantry 102, and then perform a trigonometric function to determine the distance between shaft 122 and gantry 102.

Waveguides 134 may be made of a dielectric such as glass or plastic. A relatively higher index of refraction may increase an efficiency of Cernekov photon generation. For a 6 MV treatment beam, a silica fiber could be used. Plastic or glass could be used. An index of refraction for cladding for waveguides 134 may be lower than a refractive index of the core and may be relatively low such as 1.62.

In some examples, waveguides 134 may be designed to be insertable into and removable from shaft 122. For example, shaft 122 and balloon portion 124 may be designed to be disposable. Waveguides 134 may be removed after use of treatment balloon 120 and sterilized for use in another shaft 122. Waveguides 134 may be reused for the same patient.

Waveguides 134 may be used in an endorectal balloon as mentioned above. Waveguides 134 may further be used in connection with treatment of cervical, bladder or endometrial cancer. Shaft 122 may be used in an endoscope such as for treatments relating to the lungs, stomach, colon, esophagus, small intestine, etc. Shaft 122 may be inserted into a patient through the digestive system and/or the trachea.

Figure 5:
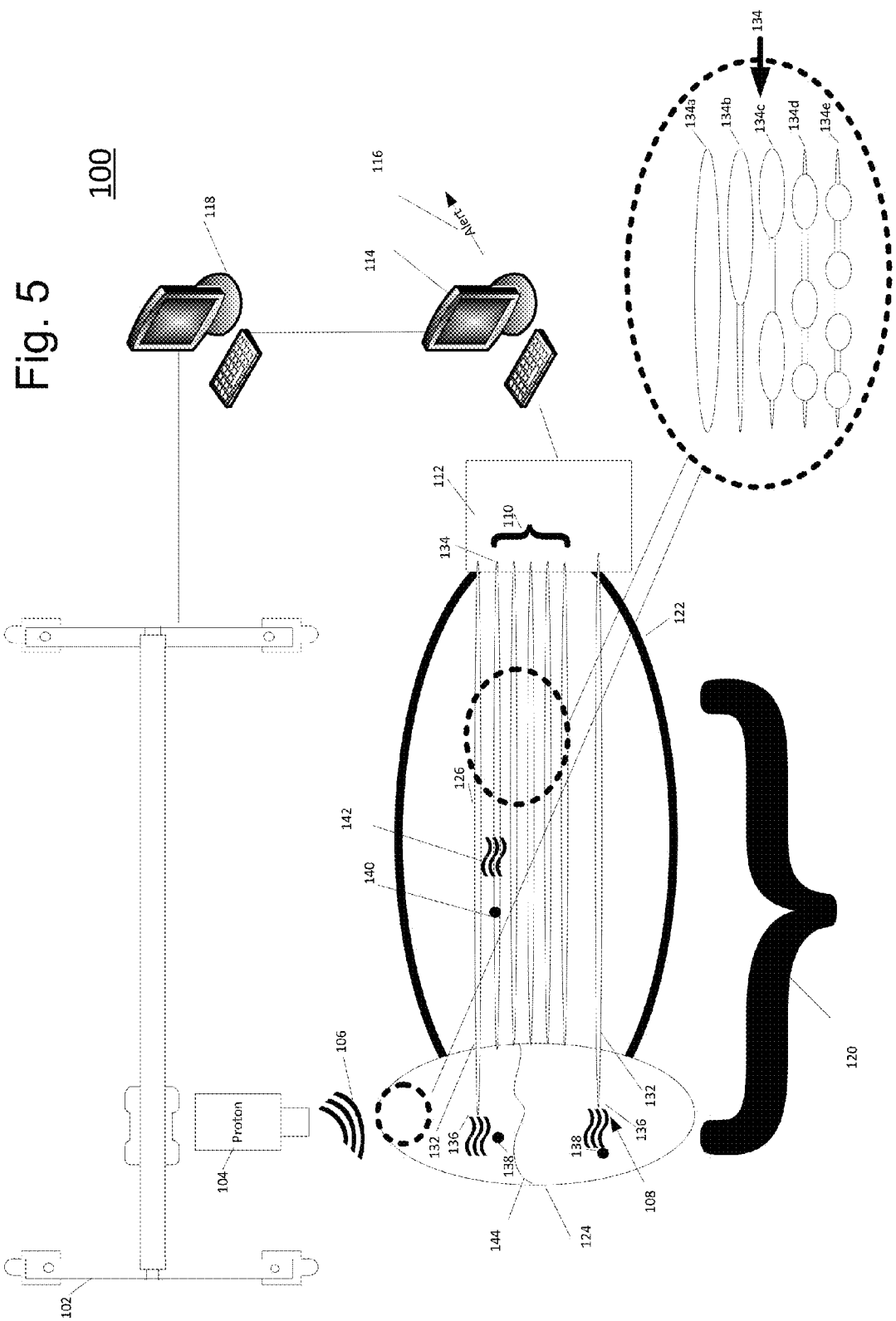
FIG. 5 is a system diagram illustrating an example treatment balloon with beam position detector.

FIG. 5 is a system diagram illustrating an example treatment balloon with beam position detector according to at least some embodiments described herein. Those components in FIG. 5 that are labelled identically to components of FIGS. 1, 2, 3, and 4 will not be described again for the purposes of clarity.

In an example, treatment source 104 may include a proton source and beam 106 may be a proton beam. Proton beam 106 may be designed to have a power to pass into and stop inside a tumor. In this example, waveguides 134, 136 may be used to detect whether beam 106 have overshot and gone past the tumor indicating that too much power is being used. A depth of dosage of proton treatment source 104 may then be adjusted. In this example, ends of waveguides 134 may be placed toward a top of balloon portion 124. For example, ends of waveguides 134 may be placed on the inside and top of balloon portion 124 so that an overshoot of beam 106 may be relatively quickly detected by processor 114. An undershoot of beam 106 may be detected by processor 114 based on a low photon count relative to an expected photon count. A zero photon count may indicate that beam 106 is too shallow, or in the wrong position.

In this example, fluid 144 in balloon portion 124 may be air. Alternatively, balloon portion 124 may be filled on a bottom with water (as shown in FIG. 5) and a top may be filled with air. In this example, having air on a top of balloon portion 124 may avoid attenuation of beam 106 before being detected by waveguides 134. Having water on the bottom of balloon portion 124 may attenuate beam 106 after waveguides 134 to protect the patient's rectum. Waveguides 134 may be made of plastic or other flexible material so that waveguides 134 may bend and change in shape as balloon portion 124 inflates and deflates.

Beam detector system 100 may be initially aligned with a patient by turning on beam 106, scanning beam 106 across a patient and detecting light waves 136, 142. A position of beam 106 may be detected based on where beam 106 falls with respect to waveguides 132 and waveguides 134. After alignment, a patient may be treated. An alignment position may be used as a reference point when gantry 102 is moved during treatment.

In an example, waveguides 134, 136 may be made of silicon carbide, silicon carbide with an epoxy, solid crystal silicon carbide, rutile ($TiO_2$) etc. For a 2 mm wide waveguide, an accuracy of position may be detected within 2 mm. Curve fitting processing may be performed by processor 114 to obtain greater accuracy.

In an example model GEANT4 software was used to model an input beam of 6 MeV photons (Gamma rays/X-Rays) pass through a cube of water (n=1.330), 2 mm per side, suspended in a vacuum. The result was 1.072141 optical photons per X-Ray photon—that is 1,072,141 optical photons for 1,000,000 X-Ray photons. In an example, waveguides may be made with LASF35, from SCHOTT GLASS with a refractive index of about 2.02. In another example, waveguides may be made of a heavy glint glass such as SF 6 1.8051 25.43 5.18 90; or SF 11 1.7847 25.76 4.74 69; LaF and LaSF Glasses such as LaF 9 1.795 28.38 4.96 81; LaSF 8 1.80741 31.61 4.87 70; LaSF N 3 1.8080 40.75 4.68 72; LaSF 11 1.80166 44.26 4.62 70; or LaSF 30 1.80200 46.47 4.90 71. The cladding may be MY-130 Series by ELECTRO OPTICAL COMPONENTS.

Among other possible benefits, positioning of a treatment beam may be detected. Undesirable affects of treatment such as impotence, incontinence, rectal bleeding, etc. may be reduced. Using a treatment balloon, an appropriate dose for treatment may be determined and more accurate dosing may be administered. Feedback may be provided to an operator or gantry with respect to positioning. Accuracy of external beam therapy may be improved even when the treated area is in motion such as when the target moves from an original position during treatment. Extra radiation need not necessarily be applied to determine a location of a treated area. A lower dosage of treatment may be used because a position of the treatment beam may be more reliably detected.

Figure 6:
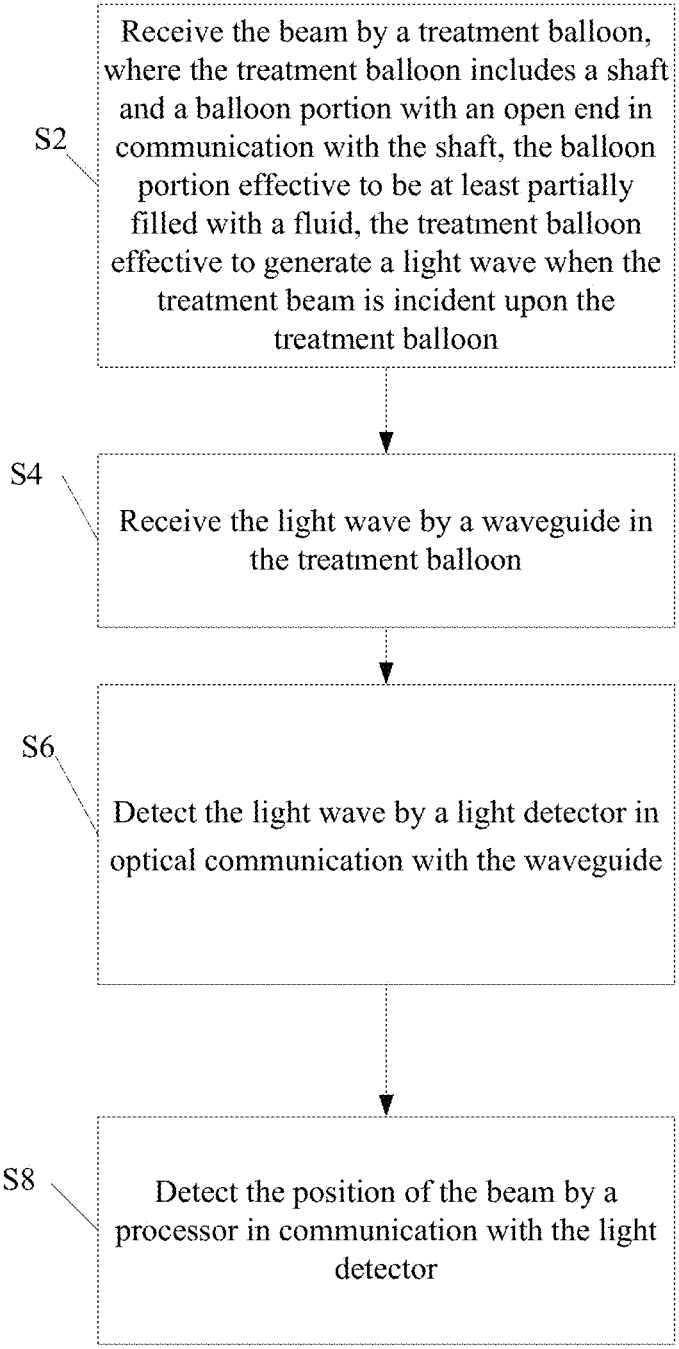
FIG. 6 depicts a flow diagram for example processes for implementing a treatment balloon with beam position detector, all arranged according to at least some embodiments described herein.

FIG. 6 depicts a flow diagram for example processes for implementing a treatment balloon with beam position detector arranged according to at least some embodiments described herein. The process in FIG. 6 could be implemented using, for example, system 100 discussed above and may be used to detect a position of beam. An example process may include one or more operations, actions, or functions as illustrated by one or more of blocks S2, S4, S6 and/or S8. Although illustrated as discrete blocks, various blocks may be divided into additional blocks, combined into fewer blocks, or eliminated, depending on the desired implementation.

Processing may begin at block S2, "Receive the beam by a treatment balloon, where the treatment balloon includes a shaft and a balloon portion with an open end in communication with the shaft, the balloon portion effective to be at least partially filled with a fluid, the treatment balloon effective to generate a light wave when the treatment beam is incident upon the treatment balloon." At block S2, the beam may be received by a treatment balloon. A first waveguide may be in the balloon portion and photons may be generated in the fluid. A second waveguide may be in the shaft and photons, may be generated with the beam is incident on the second waveguide. The second waveguide may include two or more waveguides with different thicknesses. The second waveguide may insertable into and removable from the shaft. The balloon portion and the shaft may be opaque. The second waveguide may be on a top and inside of the balloon portion.

Processing may continue from block S2 to block S4, "Receive the light wave by a waveguide in the treatment balloon." The light may be received by the first and/or the second waveguide.

Processing may continue from block S4 to block S6, "Detect the light wave by a light detector in optical communication with the waveguide." The light may be detected from the first and/or the second waveguide.

Processing may continue from block S6 to block S8, "Detect the position of the beam by a processor in communication with the light detector." The position may be detected by analyzing intensities of light in the first and second waveguides. In response to detecting the position, a processor may control the position of the beam to be moved or may stop the beam.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for detecting a position of a proton or x-ray beam, the method comprising:
    receiving the proton or x-ray beam by a treatment balloon, where the treatment balloon includes a shaft and a balloon portion with an open end in communication with the shaft, the balloon portion effective to be at least partially filled with a fluid inside of the balloon portion, the treatment balloon including a Cernekov detector effective to generate a light wave in response to detecting charged particles moving faster than the speed of light in the fluid inside of the balloon portion, wherein the charged particles are generated when the proton or x-ray beam is incident upon an outside of the treatment balloon, and the light wave is generated by the Cernekov detector inside the balloon portion;
    receiving the light wave by a waveguide in the treatment balloon;
    detecting the light wave by a light detector in optical communication with the waveguide; and
    detecting the position of the proton or x-ray beam by a processor in communication with the light detector.

2. The method of claim 1, wherein:
    the waveguide is inside the balloon portion; and
    the light wave is generated in the fluid.

3. The method of claim 1, wherein
    the waveguide is in the shaft; and
    the light wave is generated in the waveguide when the proton or x-ray beam is incident on the waveguide.

4. The method of claim 1, wherein:
    the waveguide is a first waveguide;
    the proton or x-ray beam is incident on the balloon portion;
    the first waveguide is in the balloon portion;
    a first light wave is generated in the fluid;
    a second waveguide is in the shaft and in optical communication with the light detector;
    a second light wave is generated in the second waveguide when the proton or x-ray beam is incident on the second waveguide; and
    the method further comprises detecting the position of the proton or x-ray beam based on light detected from the first waveguide and the second waveguide.

5. The method of claim 4, wherein the second waveguide includes two or more waveguides with different thicknesses.

6. The method of claim 4, wherein the first waveguide includes a third waveguide and a fourth waveguide at different positions in the balloon portion; and
    detecting the position of the proton or x-ray beam includes detecting an intensity of the light in the third waveguide and detecting an intensity of the light in the fourth waveguide.

7. The method of claim 4, wherein the second waveguide is insertable into and removable from the shaft.

8. The method of claim 1, wherein the balloon portion and the shaft are opaque.

9. The method of claim 1, wherein:
    the waveguide is a first waveguide;
    the proton or x-ray beam is incident on the balloon portion;
    the first waveguide is in the balloon portion;
    a first light wave is generated in the fluid;
    a second waveguide is on a top and inside of the balloon portion, the second waveguide is in the shaft and in optical communication with the light detector;

a second light wave is generated in the second waveguide when the proton or x-ray beam is incident on the second waveguide; and the method further comprises detecting the position of the proton or x-ray beam based on light detected from the first waveguide and the second waveguide.

10. The method of claim 9, wherein the second waveguide includes two or more waveguides with different thicknesses.

11. The method of claim 1, wherein the light detector is one of a photodiode, a photomultiplier tube, or a charged coupled diode.

12. The method of claim 1, further comprising partially filling the balloon portion with water and partially filling the balloon portion with air.

13. The method of claim 1, further comprising moving a position of the proton or x-ray beam in response to detecting the position of the beam.

14. The method of claim 1, further comprising stopping the proton or x-ray beam in response to detecting the position of the proton or x-ray beam.

15. A treatment balloon comprising:
an opaque shaft;
an opaque balloon portion with an opening in communication with the shaft, the balloon portion effective to be at least partially filled with a fluid;
at least one Cernekov detector effective to generate a light wave in response to the detection of charged particles moving faster than the speed of light in the fluid inside of the balloon portion, wherein the charged particles are generated when a proton or x-ray beam is incident upon an outside of the treatment balloon;
at least one waveguide in the treatment balloon, the waveguide effective to receive the light wave generated by the Cernekov detector inside the balloon portion; and
a light detector in optical communication with the waveguide, the light detector effective to receive and detect light from the waveguide.

16. The treatment balloon of claim 15, wherein:
the waveguide is a first waveguide in the balloon portion; and
a second waveguide is in the shaft and in optical communication with the light detector.

17. The treatment balloon of claim 16, wherein the second waveguide includes two or more waveguides with different thicknesses.

18. The treatment balloon of claim 16, wherein the first waveguide includes a third waveguide and a fourth waveguide at different positions in the balloon portion.

19. The treatment balloon of claim 16, wherein the second waveguide is insertable into and removable from the shaft.

20. The treatment balloon of claim 15, wherein:
the waveguide is a first waveguide and is in the balloon portion; and
a second waveguide is on a top and inside of the balloon portion, the second waveguide is in the shaft and in optical communication with the light detector.

21. A system effective to detect a position of a proton or x-ray beam, the system comprising:
a treatment balloon effective to receive the proton or x-ray beam, where the treatment balloon includes a shaft and a balloon portion with an open end in communication with the shaft, the balloon portion effective to be at least partially filled with a fluid inside of the balloon portion, the treatment balloon including a Cernekov detector effective to generate a light wave in response to detecting charged particles moving faster than the speed of light in the fluid inside of the balloon portion, wherein the charged particles are generated when the proton or x-ray beam is incident upon an outside of the treatment balloon, and the light wave is generated by the Cernekov detector inside the balloon portion;
a waveguide in the treatment balloon, the waveguide effective to receive the light wave;
a light detector in optical communication with the waveguide, the light detector effective to detect the light wave; and
a processor in communication with the light detector, the processor effective to detect the position of the proton or x-ray beam.

22. The system of claim 21, wherein the waveguide is inside the balloon portion.

23. The system of claim 21, wherein the waveguide is in the shaft.

24. The system of claim 21, wherein:
the waveguide is a first waveguide and is inside the balloon portion;
a second waveguide is in the shaft and in optical communication with the light detector; and
the processor is effective to detect the position of the proton or x-ray beam based on light detected from the first waveguide and the second waveguide.

25. The system of claim 24, wherein the second waveguide includes two or more waveguides with different thicknesses.

26. The system of claim 24, wherein the first waveguide includes a third waveguide and a fourth waveguide at different positions in the balloon portion; and
the processor is effective to detect the position of the proton or x-ray beam by detection of an intensity of the light in the third waveguide and detection of an intensity of the light in the fourth waveguide.

27. The system of claim 24, wherein the second waveguide is insertable into and removable from the shaft.

28. The system of claim 21, wherein the balloon portion and the shaft are opaque.

29. The system of claim 21, wherein:
the waveguide is a first waveguide and is inside the balloon portion;
a second waveguide is on a top and inside of the balloon portion, the second waveguide is in the shaft and in optical communication with the light detector; and
the processor is further effective to detect the position of the proton or x-ray beam based on light detected from the first waveguide and the second waveguide.

30. The system of claim 29, wherein the second waveguide includes two or more waveguides with different thicknesses.

31. The system of claim 29, wherein the light detector is one of a photodiode, a photomultiplier tube, or a charged coupled diode.

32. The system of claim 29, wherein the balloon portion is partially filled with water and partially filled with air.

33. The system of claim 21, wherein the processor is further effective to cause movement of a position of the proton or x-ray beam in response to a detection of the position of the proton or x-ray beam.

34. The system of claim 21, wherein the processor is further effective to stop the proton or x-ray beam in response to a detection of the position of the proton or x-ray beam.

* * * * *